US007250545B2

(12) United States Patent
Roman et al.

(10) Patent No.: US 7,250,545 B2
(45) Date of Patent: Jul. 31, 2007

(54) METHOD OF SEPARATING OLEFINS FROM MIXTURES WITH PARAFFINS

(75) Inventors: Ian C Roman, Bear, DE (US); John W Simmons, Wilmington, DE (US)

(73) Assignee: L'Air Societe Anonyme A Directoire et Conseil de Surveillance pour l'Etude at l'Exploration des Procedes Georges Claude, Paris (FR)

( * ) Notice: Subject to any disclaimer, the term of this patent is extended or adjusted under 35 U.S.C. 154(b) by 595 days.

(21) Appl. No.: 10/353,210

(22) Filed: Jan. 27, 2003

(65) Prior Publication Data

US 2004/0147796 A1 Jul. 29, 2004

(51) Int. Cl.
*C07C 7/144* (2006.01)
(52) U.S. Cl. ...................... 585/818; 585/809
(58) Field of Classification Search ................. 585/818
See application file for complete search history.

(56) References Cited

U.S. PATENT DOCUMENTS

| | | | |
|---|---|---|---|
| 4,080,744 A | 3/1978 | Manos | 34/9 |
| 4,120,098 A | 10/1978 | Manos | 34/9 |
| 4,230,463 A | 10/1980 | Henis et al. | 55/16 |
| 4,532,041 A | 7/1985 | Shuey et al. | 210/500.2 |
| 4,571,444 A | 2/1986 | Black et al. | 585/819 |
| 4,606,903 A | 8/1986 | Hafez et al. | 423/447.4 |
| 4,836,927 A | 6/1989 | Wan | 210/651 |
| 5,015,270 A | 5/1991 | Ekiner et al. | 55/16 |
| 5,034,024 A | 7/1991 | Hayes | 55/16 |
| 5,133,867 A | 7/1992 | LaFreniere | 210/651 |
| 5,605,627 A | 2/1997 | Carlsen et al. | 210/321.79 |
| 5,683,584 A | 11/1997 | Wenthold et al. | 210/500.23 |
| 5,762,798 A | 6/1998 | Wenthold et al. | 210/500.23 |
| 6,180,008 B1 | 1/2001 | White | 210/500.39 |
| 6,187,987 B1 | 2/2001 | Chin et al. | 585/819 |
| 2002/0153315 A1 | 10/2002 | Koros et al. | |

OTHER PUBLICATIONS

J.J. Krol, M. Boerrigter, G.H. Koops, Polyimide hollow fiber gas separation membranes: preparation and the suppression of plasticization in propane/propylene environments, J. Membrane Science. 184 (2001) 275-286.
C. Staudt-Bickel et al, Olefin/paraffin gas separations with 6FDA-based polyimide membranes, J. Membrane Science 170 (2000) 205-214.
Kwang-Rae Lee and Sun-Tak Hwang, Separation of propylene and propane by polyimide hollow-fiber membrane module, J. Membrane Science 73 (1992) 37-45.
International Search Report for PCT/IB 03/04966.
J. Hayashi, et al.: "*Separation of ethane/ethylene and propane/propylene systems with a carbonized BPDA-pp 'ODA polyimide membrane*", Industrial & Engineering Chemistry Research; vol. 35, No. 11—1996, pp. 4176-4181, XP 002278537; American Chemical Society, Washington.
K. Tanaka, et al.: "*Permeation and separation properties of polyimide membranes to olefins and paraffins*", Journal of Membrane Science, Elsevier Scientific Publishing Company, Amsterdam, NL; vol. 121, No. 2, Dec. 11, 1996, pp. 197-207, XP004071258.

*Primary Examiner*—Tam M. Nguyen
(74) *Attorney, Agent, or Firm*—Jeffrey C. Lew

(57) ABSTRACT

A process for the separation or concentration of olefinic hydrocarbons from mixtures of olefinic and paraffinic hydrocarbons uses a polyimide membrane. The process is well suited to separating propylene from propylene/propane mixtures. The novel method The membrane exhibits good resistance to plasticization by hydrocarbon components in the gas mixture under practical industrial process conditions.

3 Claims, No Drawings

METHOD OF SEPARATING OLEFINS FROM MIXTURES WITH PARAFFINS

This application claims priority of provisional patent application having 60/430,327 filed on Dec. 2, 2002.

FIELD OF THE INVENTION

This invention relates to a method of separating or concentrating mixtures of olefins and paraffins using a selectively permeable membrane. More specifically, it relates to a method of using certain polyimide membranes to selectively separate olefinic hydrocarbons from a gas or liquid mixture of olefinic and paraffinic hydrocarbons such as those generated by petroleum refining industries, petrochemical industries, and the like.

BACKGROUND OF THE INVENTION

Olefins, particularly ethylene and propylene, are important chemical feedstocks. Typically they are found in nature or are produced as primary products or byproducts in mixtures that contain saturated hydrocarbons and other components. Before the raw olefins can be used, they usually must be separated from these mixtures.

Currently, separation of olefin/paraffin mixtures is usually carried out by distillation. However, the similar volatilities of the components make this process costly and complicated, requiring expensive distillation columns and energy-intensive processing. Jarvelin reports that the fractional distillation of propylene/propane mixtures is the most energy-intensive distillation practiced in the United States (Harri Järvelin and James R. Fair, *Adsorptive separation of propylene/propane mixtures*, Ind. Eng. Chem. Research 32 (1993) 2201-2207). More energy conserving separation processes are needed.

Membranes have been considered for the separation of olefins from paraffins as an alternative to distillation. However, the separation is difficult largely because of the similar molecular sizes of the components. Another difficulty is that the feed stream conditions are typically close to the gas/liquid phase boundary of the mixture. Also, the membrane must operate in a hydrocarbon environment under conditions of high pressure and temperature. Such harsh conditions tend to adversely affect the durability and stability of separation performance of many membrane materials. For example, some contaminants plasticize selectively permeable membrane materials and can cause loss of selectivity and/or permeation rate. A membrane with sufficiently high olefin/paraffin selectivity, and sufficient durability in long-term contact with hydrocarbon streams under high pressure and temperature is highly desired.

Membrane materials for separating olefinic hydrocarbons from a mixture of olefinic and saturated hydrocarbons have been reported, but none can be easily or economically fabricated into membranes that offer the unique combination of high selectivity and durability under industrial process conditions.

For example, several inorganic and polymer/inorganic membrane materials with good propylene/propane selectivity have been studied. See M. Teramoto, H. Matsuyama, T. Yamashiro, Y. Katayama, *Separation of ethylene from ethane by supported liquid membranes containing silver nitrate as carrier*, J. Chem Eng. Japan 19 (1986) 1, and R. D. Hughes, J. A. Mahoney, E. F. Steigelmann, *Olefin separation by facilitated transport*, in: N. N. Li, J. M. Calo (eds.), Membrane Handbook, Van Nostrand, New York, 1992. Such materials are difficult to fabricate into practical industrial membranes. Liquid facilitated-transport membranes have been demonstrated to have attractive separation performance in the lab, but have been difficult to scale up, and have exhibited declining performance in environments typical of an industrial propylene/propane stream.

Solid polymer-electrolyte facilitated-transport membranes appear more amenable to fabrication into stable thin film membranes. See Ingo Pinnau and L. G. Toy, *Solid polymer electrolyte composite membranes for olefin/paraffin separation*, J. Membrane Science, 184 (2001) 39-48. Such a membrane is exemplified in U.S. Pat. No. 5,670,051 (Pinnau et al, 1997) wherein a silver tetrafluoroborate/poly(ethylene oxide) membrane exhibited ethylene/ethane selectivity of greater than 1000. However, these membranes are severely limited by their poor chemical stability in the olefin/paraffin industrial environment.

Carbon hollow-fiber membranes have shown promise in laboratory tests ("Propylene/Propane Separation", Product Information from Carbon Membranes, Ltd., Israel), but are vulnerable to degradation caused by condensable organics present in industrial streams. Moreover, carbon membranes are brittle and difficult to form into membrane modules of commercial relevance.

Membranes based on rubbery polymers typically have olefin/paraffin selectivity too low for an economically useful separation. For example, Tanaka et al. report that the single-gas propylene/propane selectivity is only 1.7 for a polybutadiene membrane at 50° C. (K. Tanaka, A. Taguchi, Jianquiang Hao, H. Kita, K. Okamoto, J. Membrane Science 121 (1996) 197-207) and Ito reports a propylene/propane selectivity only slightly over 1.0 in silicone rubber at 40° C. (Akira Ito and Sun-Tak Hwang, J. Applied Polymer Science, 38 (1989) 483-490).

Membranes based on glassy polymers have the potential for providing usefully high olefin/paraffin selectivity because of the preferential diffusivity of the olefin, which has smaller molecular size than the paraffin.

Glassy polymers already used in gas separation have generally shown only modest olefin/paraffin selectivity. For example, Ito has reported that films of polysulfone, ethyl cellulose, cellulose acetate and cellulose triacetate exhibit propylene/propane selectivity of 5 or less (Akira Ito and Sun-Tak Hwang, *Permeation of propane and propylene through cellulosic polymer membranes*, J. Applied Polymer Science, 38 (1989) 483-490).

U.S. Pat. No. 4,623,704 describes a process utilizing a cellulose triacetate membrane for recovering ethylene from the reactor vent of a polyethylene plant. However, the vent stream that contained 96.5% ethylene is moderately upgraded to only 97.9% in the permeate stream for recycle to the reactor.

Membrane films of poly(2,6-dimethyl-1,4-phenylene oxide) exhibited pure gas propylene/propane selectivity of 9.1 (Ito and Hwang, Ibid.) Higher selectivity has been reported by Ilinitch et al. (J. Membrane Science 98 (1995) 287-290, J. Membrane Science 82 (1993) 149-155, and J. Membrane Science 66 (1992) 1-8), but the values at higher pressure were uncertain and were accompanied by undesirable plasticization of the membrane by propylene.

Polyimide membranes have been studied extensively for the separation of gases and to some degree for the separation of olefins from paraffins. Lee et al. (Kwang-Rae Lee and Sun-Tak Hwang, *Separation of propylene and propane by polyimide hollow-fiber membrane module*, J. Membrane Science 73 (1992) 37-45) disclose a hollow fiber membrane of a polyimide that exhibited mixed-gas propylene/propane selectivity in the range of 5-8 with low feed pressure (2-4 barg). The composition of the polyimide was not disclosed.

Krol et al. (J. J. Krol, M. Boerrigter, G. H. Koops, *Polyimide hollow fiber gas separation membranes: preparation and the suppression of plasticization in propane/propylene environments*, J. Membrane Science. 184 (2001) 275-286) report a hollow fiber membrane of a polyimide composed of biphenyltetracarboxylic dianhydride and diaminophenylindane which exhibited a pure-gas propylene/propane selectivity of 12; however, the membrane was undesirably plasticized by propylene at propylene pressure as low as 1 barg.

Polyimides based on 4,4'-(hexafluoroisopropylidene) diphthalic anhydride (6FDA) and aromatic diamines have been found to provide a favorable combination of propylene permeability and propylene/propane selectivity. Permeation data for dense-film membranes of two different 6FDA-containing polyimides have been reported to have pure gas selectivity for propylene/propane in the range of 6-27. (C. Staudt-Bickel et al, *Olefin/paraffin gas separations with 6FDA-based polyimide membranes*, J. Membrane Science 170 (2000) 205-214). Higher selectivity for similar 6FDA polyimides has been reported in U.S. Pat. No. 5,749,943 (Shimazu et al); however, it is anticipated that mixed-gas selectivity at high pressure will be much lower due to plasticization by the propylene-rich feed gas.

U.S. Pat. Nos. 4,532,041; 4,571,444; 4,606,903; 4,836,927; 5,133,867; 6,180,008; and 6,187,987 disclose membranes based on a polyimide copolymer derived from the co-condensation of benzophenone 3,3',4,4'-tetracarboxylic acid dianhydride (BTDA) and a mixture of di(4-aminophenyl)methane and a mixture of toluene diamines useful for liquid separations.

U.S. Pat. Nos. 5,605,627; 5,683,584; and 5,762,798 disclose asymmetric, microporous membranes based on a polyimide copolymer derived from the co-condensation of benzophenone-3,3',4,4'-tetracarboxylic acid dianhydride (BTDA) and a mixture of di(4-aminophenyl)methane and a mixture of toluene diamines useful for liquid filtration or dialysis membranes.

U.S. Pat. No. 5,635,067 discloses a fluid separation membrane based on blends of phenylindane-containing polyimide polymers with polyimides derived from the condensation of benzophenone-3,3',4,4'-tetracarboxylic acid dianhydride (BTDA) with toluenediisocyanate (TDI) and 4,4'-methylene bisphenylisocyanate (MDI) and/or polyimides derived from the condensation of BTDA and pyromellitic dianhydride with TDI and MDI.

A significant shortcoming of published data for the separation of olefins from paraffins using membranes is the absence of data under practical industrial conditions: e.g., high feed and permeate pressure and high temperature. These are conditions under which plasticization of the membrane material could become significant and which could result in substantial decline in membrane performance over extended periods of time. In spite of the considerable efforts to provide industrially viable membranes for the separation of olefins from paraffins, none has proven to meet the performance criteria required for industrial application.

SUMMARY OF THE INVENTION

The invention is directed to a membrane separation process for separating an olefin from a mixture of olefins and paraffins comprising:

(a) providing a two-sided, selectively permeable membrane comprising a polymer or copolymer having repeating units of formula (I):

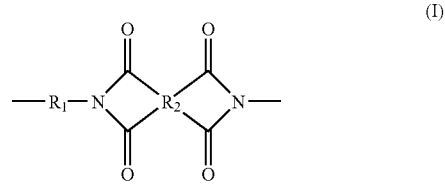

in which $R_2$ is a moiety of composition selected from the group of consisting of formula (A), formula (B), formula (C) and a mixture thereof,

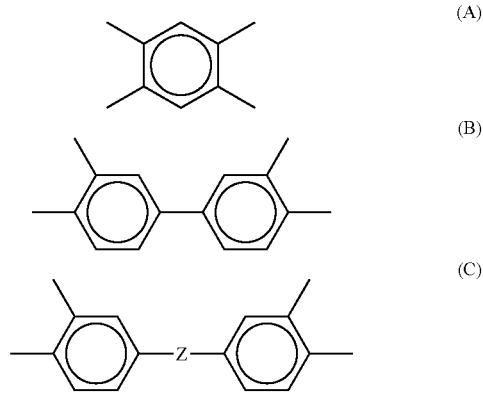

Z is a moiety of composition selected from the group consisting of formula (L), formula (M), formula (N) and a mixture thereof; and

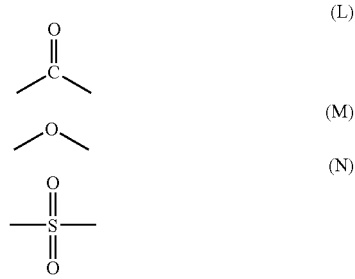

$R_1$ is a moiety of composition selected from the group consisting of formula (Q), formula (T), formula (S), and a mixture thereof,

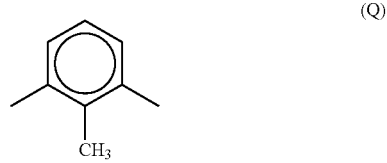

-continued

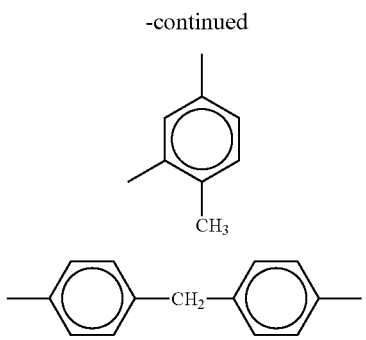

(T)

(S)

(b) contacting one side of the membrane with a feed mixture comprising an olefin compound and a paraffin compound having a number of carbon atoms at least as great as the olefin compound, (c) causing the feed mixture to selectively permeate through the membrane, thereby forming on the second side of the membrane an olefin-enriched permeate composition which has a concentration of the olefin compound greater than that of the feed mixture, (d) removing from the second side of the membrane the olefin-enriched permeate composition, and (e) withdrawing from the one side of the membrane an olefin-depleted composition.

DETAILED DESCRIPTION OF THE INVENTION

This invention is directed to a method of selectively separating olefinic hydrocarbons from paraffinic hydrocarbons using a membrane containing certain polyimide polymers, copolymers and blends thereof. The polymers which form these polyimides have repeating units as shown in the following formula (I):

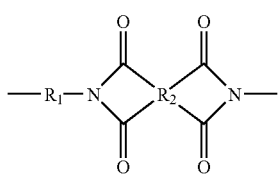

(I)

in which $R_2$ is a moiety of composition selected from the group of consisting of formula (A), formula (B), formula (C) and a mixture thereof,

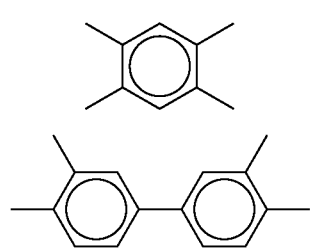

(A)

(B)

-continued (C)

Z is a moiety of composition selected from the group consisting of formula (L), formula (M), formula (N) and a mixture thereof; and (L)

(M)

(N)

$R_1$ is a moiety of composition selected from the group consisting of formula (Q), formula (T), formula (S), and a mixture thereof, (Q)

(T)

(S)

In a preferred embodiment the polyimide that forms the selective layer of the membrane has repeating units as shown in the following formula (II):

(II)

In this embodiment, moiety $R_1$ is of formula (Q) in 0-100% of the repeating units, of formula (T) in 0-100% of the repeating units, and of formula (S) in a complementary amount totaling 100% of the repeating units. A polymer of this structure is available from HP Polymer GmbH under the tradename P84 and is much preferred for use in the present invention. P84 is believed to have repeating units according to formula (II) in which $R_1$ is formula (Q) in about 16% of the repeating units, formula (T) in about 64% of the repeating units and formula (S) in about 20% of the repeating units. P84 is believed to be derived from the condensation reaction of benzophenone tetracarboxylic dianhydride (BTDA, 100 mole %) with a mixture of 2,4-toluene diisocyanate (2,4-TDI, 64 mole %), 2,6-toluene diisocyanate (2,6-TDI, 16 mole %) and 4,4'-methylene-bis(phenylisocyanate) (MDI, 20 mole %).

In another preferred embodiment, the polyimide that forms the selective layer has repeating units of compositions selected from among those shown in the following formulas (IIa and IIIb):

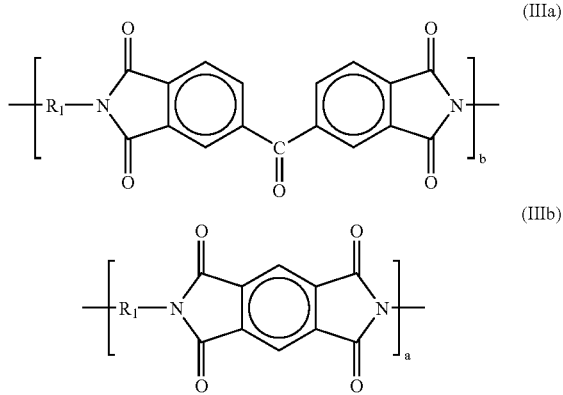

The repeating units can be exclusively of formula (IIIa) or formula (IIIb). Preferably, the repeating units are a mixture of formulas (IIIa) and (IIIb). In these embodiments, moiety $R_1$ is a composition of formula (Q) in about 1-99% of the repeating units, and of formula (T) in a complementary amount totaling 100% of the repeating units, and a is in the range of about 1-99% of the total of a and b.

A preferred polymer of this structure is available from HP Polymer GmbH under the tradename P84-HT325. P84-HT325 is believed to have repeating units according to formulas (IIIa and IIIb) in which the moiety $R_1$ is a composition of formula (Q) in about 20% of the repeating units and of formula (T) in about 80% of the repeating units, and in which a is about 40% of the total of a and b. P84-HT325 is believed to be derived from the condensation reaction of benzophenone tetracarboxylic dianhydride (BTDA, 60 mole %) and pyromellitic dianhydride (PMDA, 40 mole %) with 2,4-toluene diisocyanate (2,4-TDI, 80 mole %) and 2,6-toluene diisocyanate (2,6-TDI, 20 mole %).

In yet another preferred embodiment, the selectively permeable portion of the membrane can be formed of a material comprising a blend of the above mentioned polymers. For example, it is contemplated that a membrane can be formed from a blend comprising a first polymer having repeating units of formula (IIIa), formula (IIIb) as defined above, or a mixture of formulas (IIIa) and (IIIb) and a second polymer having repeating units of formula (II) as defined above. Greater preference is given to a membrane of a blend consisting essentially of the first and second polymers. In such preferred composition, the second polymer should constitute about 10-90 wt. % of the total of the first polymer and the second polymer.

The polyimides should be of suitable molecular weight to be film forming and pliable so as to be capable of being formed into continuous films or membranes. The polyimides of this invention preferably have a weight average molecular weight within the range of about 20,000 to about 400,000 and more preferably about 50,000 to about 300,000. The polymer can be formed into films or membranes by any of the diverse techniques known in the art. The polymers are usually glassy and rigid, and therefore, may be used to form a single-layer membrane of an unsupported film or fiber of the polymer. Such single-layer films are normally too thick to yield commercially acceptable transmembrane flux of the preferentially permeable component of the feed mixture. To be more economically practical, the separation membrane can comprise a very thin selective layer that forms part of a thicker structure. This structure may be, for example, an asymmetric membrane, which comprises a thin, dense skin of selectively permeable polymer and a thicker microporous support layer which is adjacent to and integrated with the skin. Such membranes are described, for example, in U.S. Pat. No. 5,015,270 to Ekiner.

In a preferred embodiment, the membrane can be a composite membrane, that is, a membrane having multiple layers of typically different compositions. Modern composite membranes typically comprise a porous and non-selective support layer. It primarily provides mechanical strength to the composite. A selective layer of another material that is selectively permeable, is placed coextensively on the support layer. The selective layer is primarily responsible for the separation properties. Typically, the support layer of such a composite membrane is made by solution-casting a film or spinning a hollow fiber. Then the selective layer is usually solution coated on the support in a separate step. Alternatively, hollow-fiber composite membranes can be made by co-extrusion of both the support material and the separating layer simultaneously as described in U.S. Pat. No. 5,085,676 to Ekiner.

The membranes of the invention may be housed in any convenient type of separation unit. For example, flat-sheet membranes can be stacked in plate-and-frame modules or wound in spiral-wound modules. Hollow-fiber membranes are typically potted with a thermoset resin in cylindrical housings. The final membrane separation unit can comprise one or more membrane modules. These can be housed individually in pressure vessels or multiple modules can be mounted together in a common housing of appropriate diameter and length.

In operation, a mixture of one or more olefin compounds and one or more paraffin compounds is contacted with one side of the membrane. Under a suitable driving force for permeation, such as imposing a pressure difference between the feed and permeate sides of the membrane, the olefin compounds pass to the permeate side at higher rate than the paraffin compounds of the same number of carbon atoms. That is, a three carbon olefin permeates faster than a three carbon paraffin. This produces an olefin-enriched stream which is withdrawn from the permeate side of the membrane. The olefin-depleted residue, occasionally referred to as the "retentate", is withdrawn from the feed side.

The novel process can operate under a wide range of conditions and is thus adapted to accept a feed stream supplied from diverse sources. If the feed stream is a gas that exists already at a sufficiently high, above-atmospheric pressure and a pressure gradient is maintained across the membrane, the driving force for separation can be adequate without raising feed stream pressure farther. Otherwise, the feed stream can be compressed to a higher pressure and/or a vacuum can be drawn on the permeate side of the membrane to provide adequate driving force. Preferably the driving force for separation should be a pressure gradient across the membrane of about 0.7 to about 11.2 MPa (100-1600 psi).

The novel process can accept a feed stream in either the gaseous state or the liquid state. The state of matter will depend on the composition and on the pressure and temperature of the olefin/paraffin feed stream. When the feed stream is in the liquid state, the separation can be carried out by the pervaporation mechanism. Basically, in pervaporation, components of the liquid feed mixture in contact with the membrane permeate and evaporate through the membrane, thereby separating the component in the vapor phase.

This invention is particularly useful for separating propylene from propylene/propane mixtures. Such mixtures are produced as effluent streams of olefin manufacturing operations, and in various process streams of petrochemical plants, for example. Thus in a preferred embodiment, the process involves passing a stream comprising propylene and propane in contact with the feed side of a membrane that is selectively permeable with respect to propylene and propane. The propylene is concentrated in the permeate stream and the retentate stream is thus correspondingly depleted of propylene. The membranes of this invention exhibit unexpectedly high propylene/propane selectivity which distinguishes them from prior art membranes. Furthermore, the membranes of this invention exhibit stable performance over long periods of time under conditions where membranes of the prior art degrade significantly in performance.

The fundamental steps of the separation process include contacting one side of the membrane with a feed mixture comprising an olefin compound and a paraffin compound having a number of carbon atoms at least as great as the olefin compound, causing the feed mixture to selectively permeate through the membrane, thereby forming on the second side of the membrane an olefin-enriched permeate composition which has a concentration of the olefin compound greater than that of the feed mixture, removing from the second side of the membrane the olefin-enriched permeate composition, and withdrawing from the one side of the membrane an olefin-depleted composition which has a concentration of the olefin compound less than that of the feed mixture.

This invention is now illustrated by examples of certain representative embodiments thereof, wherein all parts, proportions and percentages are by weight unless otherwise indicated. All units of weight and measure not originally obtained in SI units have been converted to SI units. The entire disclosures of U.S. patents named in the following examples are hereby incorporated by reference herein.

EXAMPLES

Example 1

Propylene/Propane Gas Separation with P84 Membrane

Asymmetric hollow-fiber membrane of P84 was spun from a solution of 32% P84, 9.6% tetramethylenesulfone and 1.6% acetic anhydride in N-methylpyrrolidinone (NMP) with methods and equipment as described in U.S. Pat. Nos. 5,034,024 and 5,015,270. The nascent filament was extruded at a rate of 180 cm$^3$/hr through a spinneret with fiber channel dimensions of outer diameter 559 µm and inner diameter equal to 254 µm at 75° C. A fluid containing 85% NMP in water was injected into the bore of the fiber at a rate of 33 cm$^3$/hr. The nascent fiber traveled through an air gap of 5 cm at room temperature into a water coagulant bath at 24° C. and the fiber was wound up at a rate of 52 m/min.

The water-wet fiber was washed with running water at 50° C. to remove residual solvent for about 12 hours and then sequentially exchanged with methanol and hexane as taught in U.S. Pat. Nos. 4,080,744 and 4,120,098, followed by vacuum drying at room temperature for 30 minutes. After that the fibers were dried at 100° C. for one hour. Samples of fiber were formed into four test membrane modules of 52 fibers each. The fiber in the modules was treated to seal defects in the separating layer with a method similar to the method described in U.S. Pat. No. 4,230,463. The fiber was thus contacted with a solution of 2% wt. 1-2577 Low-VOC Conformal Coating (Dow Corning Corporation) in 2,2,4-trimethylpentane for 30 minutes and then dried.

The modules were measured in permeation of a feed of mixed propylene/propane (50:50 mole %). The feed mixture was provided in the vapor state by controlling the feed pressure at 2.8 MPa (400 psig) and the feed temperature at 90° C. The feed mixture was supplied to contact the outside of the fibers and the permeate stream was collected at atmospheric pressure. The permeate flowrate was measured by volumetric displacement with bubble flowmeters. The feed flowrate was maintained at greater than twenty times the permeate flowrate. This rate was high enough that the composition on the feed side remained roughly constant while the feed mixture permeated the membrane. This was done to simplify calculation of the membrane permeation performance. The composition of the permeate stream was measured by gas chromatography with a flame ionization detector. The average permeate composition was 92.2% propylene and 7.8% propane.

The performance of the membrane was expressed in terms of propylene permeance and propylene/propane selectivity. The permeance is the flowrate of propylene across the membrane normalized by the membrane surface area and the propylene partial pressure difference across the membrane. It is reported in gas permeation units ("GPU"). One GPU equals $10^{-6}$ cm$^3$(at standard temperature and pressure "STP")/(sec·cm$^2$·cmHg). The propylene/propane selectivity is the ratio of the permeance of propylene divided by the permeance of propane. The performance of the four modules is shown in Table 1.

TABLE I

| Propylene Permeance (1) GPU | Propylene/Propane selectivity (1) |
|---|---|
| 1.3 | 12.0 |
| 0.97 | 12.5 |
| 1.4 | 12.9 |
| 1.3 | 13.1 |

(1) measured after 24 hours

Example 2

Propylene/Propane Gas Separation with P84 Non-Posttreated Membrane

A sample of the fiber from Example 1 was processed and formed into a test module as in Example 1 except that the fiber was not treated to seal defects in the separating layer. The propylene permeance was 1.7 GPU and the propylene/propane selectivity was 7.5. Although the selectivity was lower than the selectivity of the treated fiber of Example 1, it was high enough to suggest that the P84 fiber with acceptable performance characteristics can be produced as an asymmetric membrane without the sealing posttreatment.

Example 3

Propylene/Propane Gas Separation with P84 Membrane

Asymmetric hollow-fiber membrane of P84 was prepared as in Example 1 with the following two changes: (a) the water-bath temperature was lowered to 8° C. and (b) the spinneret temperature was increased to 87° C. The fiber was washed, dried and built into test modules and tested in permeation of a 50:50 mole % mixed propylene/propane feed mixture as in Example 1. The propylene permeance was 0.61 GPU and the propylene/propane selectivity was 15.

Example 4

Durability of P84 Membrane in Propylene/Propane Gas Separation with P84 Membrane Asymmetric hollow-fiber membrane of P84 similar to the fiber of Example 3 was tested for duration of 4 days at 90° C. with a 50:50 mole % feed mixture of propylene/propane at 2.8 MPa (400 psig). The test was designed to simulate commercial operating conditions. Results are shown in Table II. No decline in selectivity was observed. A slight decline was observed in propylene permeance, which stabilized after the second day.

TABLE II

| Time | Feed Pressure MPa (psig) | Propylene/Propane Selectivity | Propylene permeance GPU |
|---|---|---|---|
| 4 hours | 1.7 (250) | 13 | 0.76 |
| 1 day | 1.7 (250) | 13 | 0.96 |
| 2 days | 1.7 (250) | 13 | 0.73 |
| 3 days | 2.8 (400) | 12 | 0.61 |
| 4 days | 2.8 (400) | 14 | 0.61 |

Example 5

Propylene/Propane Liquid Feed Separation with P84 Membrane

One of the modules of Example 1 was tested using a 50:50 mole % feed mixture of propylene/propane. Feed pressure and temperature were controlled at 2.8 MPa (400 psig) and 50° C., respectively, to place the feed mixture in the liquid state. The permeate was withdrawn at atmospheric pressure, therefore the permeate was in the vapor phase. For this type of separation the concentration difference across the membrane is usually considered to be the driving force for separation instead of the partial pressure difference as used in gas or vapor permeation. For comparison of the results of this Example with permeation under vapor state feed conditions, the simplifying mathematical treatment described in J. G. Wijmans and R. W. Baker, *A simple predictive treatment of the permeation process in pervaporation*, J. Membrane Science 79 (1993) 101-113) was applied. Such analysis assumes that the liquid feed evaporates to produce a saturated vapor phase on the feed side of the membrane and then permeates through the membrane driven by a partial pressure gradient. This analysis provides a mathematical model that includes terms for feed-side and permeate-side vapor pressures and permeance and selectivity comparable to those used in the separation of gaseous state feed mixtures. The model also contains a term related to the liquid-vapor equilibrium. With the feed mixture of 50:50 mole % propylene/propane in the liquid state, the membrane produced a permeate stream of 93% propylene. By application of the model, it was determined that the propylene permeance was 0.46 GPU and the propylene/propane selectivity was 16. In separate testing with feed mixture of the same composition in the vapor state at 2.8 MPa (400 psig) and 90° C., the propylene permeance was 0.95 GPU and the propylene/propane selectivity was 13. This shows that the membrane of P84 can be useful for separation service for liquid propylene/propane.

Example 6

Propylene/Propane Gas Separation with a Membrane of P84 Blended with P84-HT325

Asymmetric hollow-fiber membrane of a 1:1 blend of P84 and P84-HT325 was spun from a solution of 16% P84, 16% P84-HT325, 9.6% tetramethylene sulfone and 1.6% acetic anhydride in NMP by the process described in Example 1. The spinning conditions and equipment were similar except that the spinneret temperature was 85° C., the bath temperature was 8° C. and the air gap was 10 cm. The fiber was formed into a module which was tested for permeation of a propylene/propane (50:50 mole %) feed mixture as in Example 1. The permeation performance was 1.9 GPU propylene permeance and 11.9 propylene/propane selectivity.

Example 7

Propylene/Propane Liquid Feed Separation with a Membrane of P84 blended with P84-HT325

The module of 1:1 blend of P84 and P84-HT325 of Example 6 was tested with 50:50 mole % feed mixture of propylene/propane. The feed mixture was maintained in the liquid state by applying the conditions described in Example 5, i.e., the feed pressure was 2.8 MPa (400 psig) and the temperature was 50° C. The permeate was withdrawn as a vapor at atmospheric pressure.

The membrane produced a permeate with 93.6% propylene; the propylene permeance was 0.6 GPU and the propylene/propane selectivity was 15.5. This shows that the membrane of 1:1 blend of P84 and P84-HT325 can provide useful separation with liquid propylene/propane feed.

Example 8

Propylene/Propane Liquid Feed Separation with a Membrane of P84 blended with P84-HT325

The test in Example 7 (i.e., with membrane of 1:1 blend of P84 and P84-HT325) was continued for a duration of 100 hours, to assess membrane performance stability under simulated commercial conditions. Results are shown in Table III. No significant decline was observed.

TABLE III

| Time Hours | Propylene/Propane Selectivity | Propylene Permeance GPU |
|---|---|---|
| 24 | 15.5 | 0.56 GPU |
| 60 | 15.9 | 0.59 GPU |
| 84 | 15.6 | 0.67 GPU |
| 110 | 15.8 | 0.67 GPU |

Example 9

Propylene/Propane Gas Separation with P84 Dense Film Membrane

A thin dense film of P84 polymer was cast from a solution comprising 20% P84 in NMP. The film was dried at 200° C. in a vacuum oven for four days. A sample of the polymer film was tested in a modified 47-mm ultrafiltration style permeation cell (Millipore), using a feed mixture of 50:50 mole % propylene/propane at 2.8 MPa (400 psig) pressure and 90° C. temperature. The permeate pressure was 2-5 mm Hg. The feed flowrate was high enough to ensure low conversion of the feed into permeate so that the composition on the feed side was constant. The compositions of the feed and permeate streams were measured by gas chromatography with a flame ionization detector. The permeate flowrate was determined from the increase in pressure over time in the fixed-volume permeate chamber of the permeation cell.

The permeation performance of the polymer is characterized by the two parameters: propylene permeability and propylene/propane permselectivity. The permeability is the flowrate of propylene across the film normalized by the film surface area and film thickness and by the propylene partial pressure difference across the film. Units of permeability are Barrers. One Barrer equals $10^{-10}$ cm$^3$ (STP)·cm/(sec·cm$^2$·cm Hg). The propylene/propane permselectivity is the ratio of the propylene and propane permeabilities. The propylene permeability of the P84 film at 90° C. and 2.8 MPa (400 psig) was 0.24 Barrers; and the propylene/propane permselectivity was 15.5. The permselectivity was in good agreement with the selectivity measured with hollow-fiber membranes of P84 polymer.

Example 10

Propylene/Propane Separation with a Membrane of TDI+BTDA:BPDA(1:1)

A dense film of a copolymer of toluenediisocyanate (TDI, a mixture of 20% 2,6-toluenediisocyanate and 80% 2,4-toluenediisocyanate) and a 1:1 mixture of benzophenone-3, 3',4,4'-tetracarboxylic acid dianhydride (BTDA) with 3,3', 4,4'-biphenyl tetracarboxylic dianhydride (BPDA) was tested in permeation with 50:50 mole % mixed propylene/propane feed at 2.8 MPa (400 psig) and 90° C. as in Example 9. The propylene permeability of the film was 0.48 Barrers and the propylene/propane permselectivity was over 16.

Comparative Example 1

Polypropylene/Propane Separation with a Traditional Composition Fiber Membrane Samples of composite hollow-fiber membrane of Matrimid® 5218 a copolymer of 5,x-amino-(4-aminophenyl)-1, 1,3 trimethyl indane and 3,3',4,4'-benzophenone tetracarboxylicdianhydride (Vantico, Inc.) were tested in permeation over a 72-hour period with a feed mixture of 50:50 mole % propylene/propane at 1.7 MPa (250 psig) and 90° C. as in Example 1. The purpose of the test was to determine the membrane performance stability under simulated commercial conditions. This membrane, described in U.S. Pat. No. 5,468,430 is a commercial gas-separation membrane produced by MEDAL, LP. Results of the test are shown in Table IV.

TABLE IV

| Time hours | Propylene/Propane Selectivity | Propylene permeance GPU |
|---|---|---|
| 2 | 5.5 | 9.0 |
| 24 | 7.0 | 4.8 |
| 48 | 7.1 | 4.0 |
| 72 | 7.2 | 3.8 |

As apparent from these results, the membrane exhibited low selectivity and lost greater than 50% of its initial permeance during the test, unlike the membranes of this invention.

Comparative Example 2

Propylene/Propane Separation with a Polyaramid Membrane

Samples of asymmetric hollow-fiber membrane made from a blend of two aromatic polyamides were tested in permeation of a feed mixture of 50:50 mole % propylene/propane at 2.8 MPa (400 psig) and 90° C. as in Example 1. This membrane is described in U.S. Pat. No. 5,085,774 (Example 15). The fiber was spun at a draw ratio of 7.3. It is an established gas-separation membrane applied in the separation of hydrogen from mixtures with hydrocarbons or carbon monoxide. It exhibited a propylene permeance of 0.23 GPU and a propylene/propane selectivity of 9.5. This performance was less than that of the novel membranes having composition of formula (I). This result was unexpected because the membrane of aromatic polyamide has very high selectivity in separations of other mixtures, for example a selectivity of higher than 200 for $H_2/CH_4$ at 90° C.

Although specific forms of the invention have been selected for illustration in the preceding description which is drawn in specific terms for the purpose of describing these forms of the invention fully and amply for one of average skill in the pertinent art, it should be understood that various substitutions and modifications which bring about substantially equivalent or superior results and/or performance are deemed to be within the scope and spirit of the following claims.

What is claimed is:

1. A membrane separation process for separating an olefin from a mixture of olefins and paraffins comprising:
   (a) providing a two-sided, selectively permeable membrane comprising a polymer or copolymer having repeating units of formula (II)

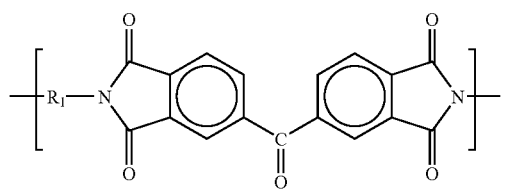

(II)

in which $R_1$ is a moiety of composition selected from the group consisting of formula (Q), formula (T), and formula (S),

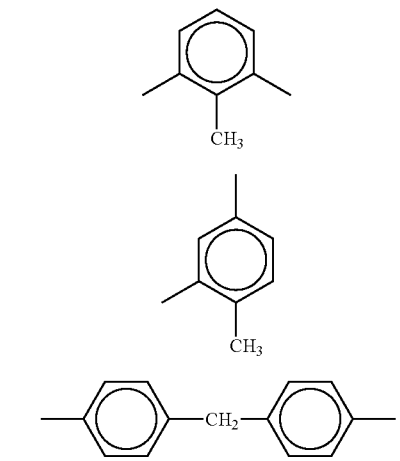

(Q)

(T)

(S)

in which the moiety $R_1$ is of formula (Q) in about 16% of the repeating units, of formula (T) in about 64% of the repeating units, and of formula (S) in about 20% of the repeating units
   (b) contacting one side of the membrane with a feed mixture comprising an olefin compound and a paraffin compound having a number of carbon atoms at least as great as the olefin compound,
   (c) causing the feed mixture to selectively permeate through the membrane, thereby forming on the second side of the membrane an olefin-enriched permeate composition which has a concentration of the olefin compound greater than that of the feed mixture,
   (d) removing from the second side of the membrane the olefin-enriched permeate composition, and
   (e) withdrawing from the one side of the membrane an olefin-depleted composition.

2. A membrane separation process for separating an olefin from a mixture of olefins and paraffins comprising:
   (a) providing a two-sided, selectively permeable membrane comprising a polymer or copolymer in which the repeating units comprise moieties of composition selected from the group consisting of formula (IIIa), formula (IIIb) and mixtures thereof

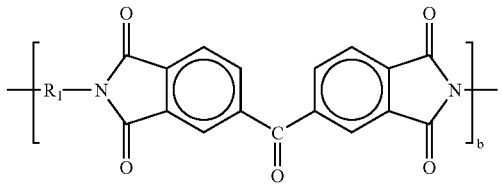

(IIIa)

(IIIb)

in which $R_1$ is a moiety of composition selected from the group consisting of formula (Q), and formula (T),

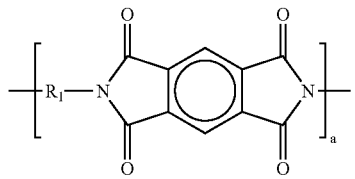

(Q)

(T)

in which moiety $R_1$ is of formula (Q) in about 1-99% of the repeating units, and of formula (T) in a complementary amount totaling 100% of the repeating units, and
   in which a is in the range of about 1-99% of a+b,
   (b) contacting one side of the membrane with a feed mixture comprising an olefin compound and a paraffin compound having a number of carbon atoms at least as great as the olefin compound,
   (c) causing the feed mixture to selectively permeate through the membrane, thereby forming on the second side of the membrane an olefin-enriched permeate composition which has a concentration of the olefin compound greater than that of the feed mixture,
   (d) removing from the second side of the membrane the olefin-enriched permeate composition, and
   (e) withdrawing from the one side of the membrane an olefin-depleted composition.

3. The process of claim 2, in which the moiety R1 is of formula (Q) in about 20% of the repeating units and of formula (T) in about 80% of the repeating units, and in which a is about 40% of a+b.

* * * * *